United States Patent
Stangenes et al.

(10) Patent No.: US 9,326,756 B2
(45) Date of Patent: May 3, 2016

(54) TRANSSEPTAL CATHETERIZATION ASSEMBLY AND METHODS

(75) Inventors: Todd Stangenes, Minneapolis, MN (US); Brian Schmidt, Bloomington, MN (US); Xuan Khieu, Maple Grove, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1798 days.

(21) Appl. No.: 11/646,525

(22) Filed: Dec. 28, 2006

(65) Prior Publication Data

US 2007/0270751 A1    Nov. 22, 2007

Related U.S. Application Data

(60) Provisional application No. 60/800,854, filed on May 17, 2006.

(51) Int. Cl.
| | |
|---|---|
| *A61M 5/178* | (2006.01) |
| *A61B 17/00* | (2006.01) |
| *A61B 17/34* | (2006.01) |
| *A61B 18/00* | (2006.01) |
| *A61B 19/00* | (2006.01) |
| *A61M 25/00* | (2006.01) |
| *A61M 25/06* | (2006.01) |

(52) U.S. Cl.
CPC ....... *A61B 17/00234* (2013.01); *A61B 17/3478* (2013.01); *A61B 2017/0046* (2013.01); *A61B 2017/00247* (2013.01); *A61B 2018/00392* (2013.01); *A61B 2019/304* (2013.01); *A61M 25/0084* (2013.01); *A61M 2025/0681* (2013.01)

(58) Field of Classification Search
CPC ............... A61B 17/00234; A61B 17/3478; A61B 2017/0046; A61B 2017/00247; A61B 2019/304; A61B 2018/00392; A61M 25/0084; A61M 2025/0681
USPC ............... 606/185, 191, 108, 167, 170, 194; 604/335, 323, 533, 164.12; 600/1, 498, 600/159; 607/116
See application file for complete search history.

(56) References Cited

U.S. PATENT DOCUMENTS

| | | | |
|---|---|---|---|
| 4,561,445 A | | 12/1985 | Berke et al. |
| 5,224,470 A | * | 7/1993 | Schnepp-Pesch et al. ..... 600/566 |
| 5,273,532 A | * | 12/1993 | Niezink et al. ................. 604/62 |
| 5,281,218 A | | 1/1994 | Imran |

(Continued)

FOREIGN PATENT DOCUMENTS

| | | |
|---|---|---|
| WO | 95-10319 A1 | 4/1995 |
| WO | 2006039531 A | 4/2006 |

OTHER PUBLICATIONS

International European Search Report Application No. 07009812.4-1526 dated Feb. 29, 2008 (9 pages).

(Continued)

*Primary Examiner* — Tuan V Nguyen
*Assistant Examiner* — Tin Nguyen
(74) *Attorney, Agent, or Firm* — Wiley Rein LLP

(57) ABSTRACT

Improved hand assemblies and methods combining a number of the separate known devices used in transseptal catheterization procedures, including sheaths, dilators, and needle assemblies (including a puncture device and a stylet, for example). The hand assemblies provide cooperating members that reduce the overall complexity and increase safety of transseptal catheterization procedures.

19 Claims, 13 Drawing Sheets

(56) References Cited

U.S. PATENT DOCUMENTS

| | | | |
|---|---|---|---|
| 5,292,310 A | 3/1994 | Yoon | |
| 5,330,443 A | 7/1994 | Powles et al. | |
| 5,403,311 A | 4/1995 | Abele et al. | |
| 5,405,376 A | 4/1995 | Mulier et al. | |
| 5,431,649 A | 7/1995 | Mulier et al. | |
| 5,507,802 A | 4/1996 | Imran | |
| 5,628,734 A | 5/1997 | Hatafalvi | |
| 5,807,395 A | 9/1998 | Mulier et al. | |
| 5,906,613 A | 5/1999 | Mulier et al. | |
| 5,910,129 A | 6/1999 | Koblish | |
| 5,928,208 A * | 7/1999 | Chu et al. | 604/523 |
| 5,945,070 A | 8/1999 | Kath | |
| 5,992,899 A * | 11/1999 | Strowe | 285/93 |
| 6,048,329 A | 4/2000 | Thompson et al. | |
| 6,053,904 A | 4/2000 | Scribner | |
| 6,071,274 A | 6/2000 | Thompson et al. | |
| 6,071,279 A | 6/2000 | Whayne et al. | |
| 6,076,012 A | 6/2000 | Swanson et al. | |
| 6,187,019 B1 * | 2/2001 | Stefanchik et al. | 606/144 |
| 6,200,315 B1 | 3/2001 | Gaiser et al. | |
| 6,203,525 B1 | 3/2001 | Whayne et al. | |
| 6,224,588 B1 * | 5/2001 | Jentzen | 604/533 |
| 6,330,473 B1 | 12/2001 | Swanson et al. | |
| 6,402,746 B1 | 6/2002 | Whayne et al. | |
| 6,454,758 B1 | 9/2002 | Thompson et al. | |
| 6,595,958 B1 | 7/2003 | Mickley | |
| 6,958,056 B2 | 10/2005 | Kadziauskas | |
| 7,025,766 B2 | 4/2006 | Whayne et al. | |
| 2002/0099335 A1 * | 7/2002 | Zohmann | 604/198 |
| 2003/0028147 A1 | 2/2003 | Aves et al. | |
| 2003/0153874 A1 * | 8/2003 | Tal | 604/164.1 |
| 2004/0039338 A1 * | 2/2004 | Lee et al. | 604/164.12 |
| 2004/0092879 A1 * | 5/2004 | Kraus et al. | 604/158 |
| 2005/0020988 A1 * | 1/2005 | Woehr et al. | 604/243 |
| 2005/0085883 A1 * | 4/2005 | Ollivier et al. | 607/116 |
| 2005/0149097 A1 | 7/2005 | Regnell et al. | |
| 2005/0222554 A1 | 10/2005 | Wallace et al. | |
| 2006/0095022 A1 | 5/2006 | Moll et al. | |
| 2006/0100610 A1 | 5/2006 | Wallace et al. | |

OTHER PUBLICATIONS

"Sterile hypodermic needles for single use", ISO 7864, Third Edition May 15, 1993.

\* cited by examiner

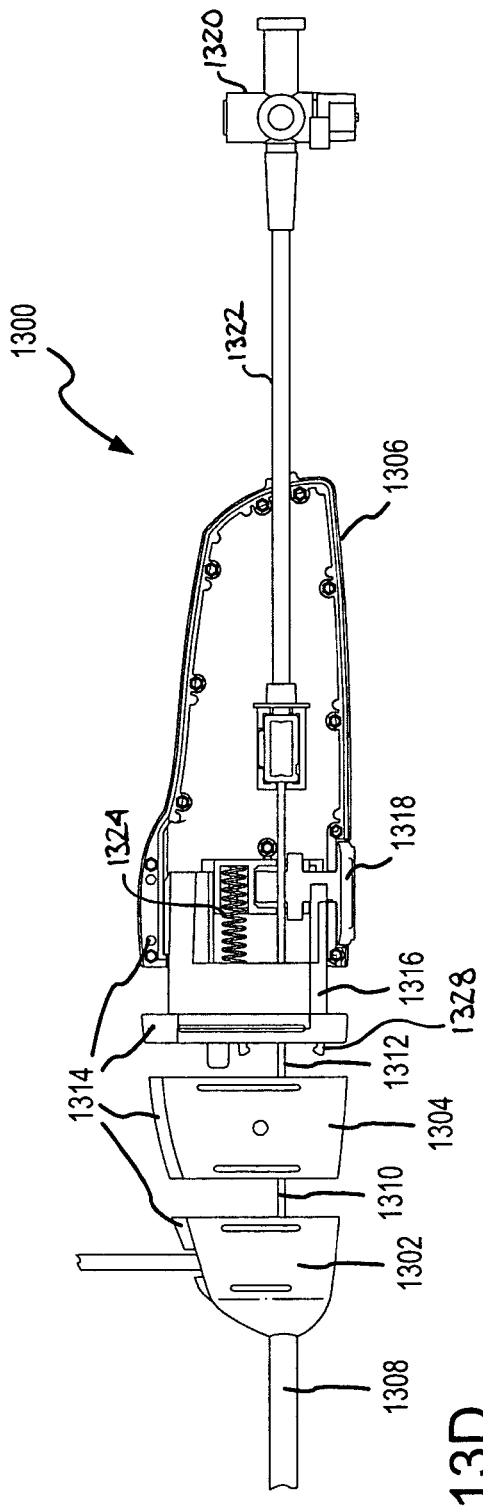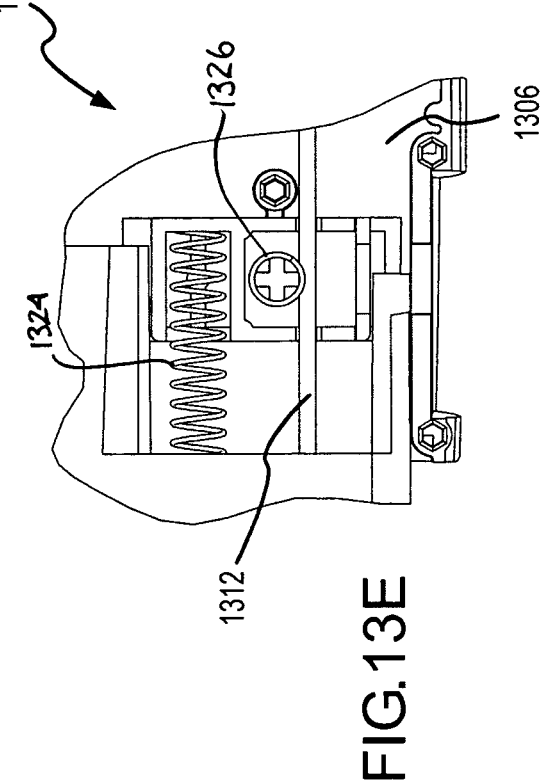
FIG.13D
FIG.13E

TRANSSEPTAL CATHETERIZATION ASSEMBLY AND METHODS

CROSS REFERENCE TO RELATED APPLICATIONS

This application claims the benefit of U.S. provisional application No. 60/800,854, filed 17 May 2006, which is hereby incorporated by reference as fully set forth herein.

BACKGROUND OF THE INVENTION a. Field of the Invention

The instant invention relates to assemblies and methods for puncturing, or piercing, tissue within the body, including, for example, transseptal access systems and methods for accessing the left atrium from the right atrium by crossing the fossa ovalis. In particular, the instant invention is directed toward medical devices used with catheter assemblies in cardiology procedures that require tissue punctures, or piercings, such as transseptal punctures. More specifically, the instant invention relates to improved hand assemblies and methods combining a number of the separate devices used in transseptal catheterization procedures, including sheaths, dilators, and needle assemblies (including a puncture device and a stylet, for example). The hand assemblies provide cooperating members that reduce the overall complexity and increase safety of complicated and dangerous transseptal catheterization procedures.

b. Background Art

The human heart includes a right ventricle, a right atrium, left ventricle and left atrium. The right atrium is in fluid communication with the superior vena cava and the inferior vena cava. The tricuspid valve separates the right atrium from the right ventricle. The right atrium is separated from the left atrium by the interatrial septum.

A wide variety of diagnostic and therapeutic procedures have been developed in which a catheter is transluminally advanced within a guide sheath or over a guidewire into various chambers and across valves of the heart. The most difficult chamber of the heart to access with a catheter is the left atrium. Access to the left atrium through the pulmonary artery is not possible. Approaches from the left ventricle are difficult, may cause arrhythmias and may present difficulty in obtaining stable catheter positioning. Accordingly, the most common approach used by electrophysiologists to gain access to the left atrium is through puncture of the interatrial septum.

The objectives of left atrial access can be either diagnostic or therapeutic. One therapeutic use is electrophysiological intervention, e.g., left atrial ablation. Catheter ablation involves the placement of energy (typically RF) through a catheter, into various locations of the heart to eradicate inappropriate electrical pathways affecting the heart function. When these locations are in the left atrium, the catheter through which the RF generator is placed typically is itself placed through transseptal catheterization.

In most cases, transseptal catheterization is facilitated with three separate transseptal tools; a sheath, dilator, and a needle. For example, FIG. 1 shows the details of the proximal end of current transseptal tools, which include: a sheath 10 and a sheath hub 12; a dilator 14 and a dilator hub 16; and a needle assembly 22 comprising a needle 18 and needle hub 20. The conventional approach for transseptal catheterization follows a number of steps. First, a guidewire is introduced into the femoral vein (or other pathway of choice) and is manipulated into the superior vena cava (SVC). Second, a sheath 10 typically having a dilator 14 disposed therein are inserted over the proximal end of the guidewire and are fed into the SVC. At this point, the guidewire is removed. Third, a needle assembly 22 (potentially including a stylet 24) is advanced through the inner lumen of the dilator 14 until the distal end of the stylet 24 or needle 18 is just inside the distal end of the dilator 14. The stylet 24 typically extends a portion beyond the distal end of the needle 18.

In most cases, the physician visually determines the point at which the stylet 24 and/or needle assembly 22 is just inside the distal end of the dilator 14 by examining the space between the proximal end of the dilator hub 16 and the distal end of the needle hub 20 (the distance "X" in FIG. 1). As a rule of thumb, it is typically understood that the stylet 24 is in the appropriate position when the dilator hub 16 is separated from the needle hub 20 by "two finger-widths" of the physician. Clearly, this method is an imprecise approximation of the position and lends itself to adjustment errors and difficulties. Alternatively, the physician may use fluoroscopy to verify the position of the stylet 24 or needle 18. This method, however adds significant expense and complications to the procedure.

Once the needle assembly 22 is deemed in the appropriate position, the stylet 24 is typically removed from the inner lumen of the needle 18 and discarded. At this point, the physician then advances the needle assembly 22 forward until the distal end of the needle 18 is just inside the distal end of the dilator 14. As shown in FIG. 1, this distance is again visually determined and approximated by examining the space between the needle hub 20 and the dilator hub 16. Alternatively, the physician may use other complicated diagnostic methods such as fluoroscopy.

In this position, with the needle 18 still contained within the distal end of the dilator 14, the assembly 22 is pulled along the septal wall of the right atrium until it is proximate the fossa ovalis. The needle assembly 22 is then advanced forward by the physician through the dilator 14 to puncture the septal wall. Upon confirmation of the puncture, the dilator 14 and sheath 10 can then be fed through the septal wall over the needle assembly 22, thereby accessing the left atrium.

Despite clinical acceptance of a wide variety of procedures which require access to the left atrium, significant room for improvement remains in the actual access technique and mechanisms designed to facilitate such access. A number of risks, in addition to the risks associated with normal heart catheterization, are inherent in transseptal catheterization. For example, a major risk present stems from the use of known transseptal devices, which typically have a puncture device, or needle, that can be inadvertently exposed during the procedure. For this reason, there is a need to provide a puncture assembly where the puncture device, referred to in the embodiments of the present application as a needle assembly, is safely maintained at a substantially fixed location within the dilator until the assembly is positioned at the puncture point of the septum.

Moreover, the known assemblies are cumbersome and difficult to operate. Thus, a significant drawback with current transseptal tools lies in the fact that the tools are effectively three separate components that operate independently of one another. This independence introduces significant difficulties to a user in that they must all be manipulated, or held in place, independently through manual efforts of the user. It would be highly desirable to provide for a cooperating handle assembly combining these components, with the addition of mechanical safety features, to provide improved safety and utility in connection with accepted medical procedures. In particular, it is desirable to mechanize the process for proper positioning of the needle, dilator, sheath, and stylet during the procedure and to further provide safety features to avoid unnecessary punctures and similar mistakes during operation.

BRIEF SUMMARY OF THE INVENTION

The embodiments of the present invention improve upon the design of current transseptal tools (including the sheath, dilator and needle assemblies) through inclusion of additional safety mechanisms and predetermined advancement mechanisms in an easy-to-use cooperative handle assembly to improve and simplify known transseptal procedures. The embodiments of the present invention may include any number or combination of the following design aspects. For purposes of explanation, the present invention is described in accordance with transseptal puncture methods, but it is contemplated that the present invention is adaptable and useful for any number of applications where tissue within the body is accessed through a catheter-type mechanism and is punctured or pierced in connection with any particular medical procedure.

Single Handle Assembly

Throughout the entire transseptal procedure, conventional tools and devices require a physician to maintain control over a number of physically separate devices, typically spaced at given distances apart from each other. Importantly, it is necessary to further maintain the orientation of the devices with respect to each other throughout a particular procedure. The present invention provides a cooperative handle assembly configured to allow for easy, efficient manipulation of the various components, and also to provide for ease in management of location and orientation of the components. When all components are placed together, the result is a single handle assembly for facilitating manipulation. The particular features of the handle assembly are discussed briefly below.

Stylet Stop Mechanism

A stylet is often used to assist in advancement of the needle into the dilator. The stylet also serves to prevent kinking of the needle. The stylet typically extends beyond the distal portion of the needle assembly. The present invention includes a mechanical stylet stop either near the distal end of the dilator, or within the handle mechanism to prevent advancement of the needle until the stylet is removed. Alternatively, the stop may push the stylet back, out of the needle, as the distal tip of the stylet reaches the distal end of the dilator. This feature prevents unintentional advancement of the stylet out of the dilator which may cause harm to the patient. This stop further eliminates the need for the physician to visually gauge the separation between the needle hub and the dilator hub, thereby simplifying and improving the reliability of transseptal procedures. In use, the stylet is often removed from the assembly after the needle is advanced into the dilator.

Needle Stop Mechanism

After removing the stylet, the needle is advanced through the sheath and the dilator until the distal end of the needle is just inside the distal end of the dilator. The present invention provides a stop mechanism to provide tactile feedback to the physician when the needle reaches this point. This mechanical stop also prevents unintentional advancement of the needle out of the dilator which may cause harm to the patient during use. For example, in FIG. 2, this feature includes an extension of the needle hub configured to include a spacer having a length (X) that corresponds to the distance the needle extends from the dilator at the distal end of the assembly when fully extended. The needle stop mechanism is held in place by a locking mechanism that can be activated by a button, or other activation device.

Needle Advance Mechanism

After reaching the desired location for puncture, the physician can activate a button that is mechanically connected to the needle stop. The button then allows for advance of the needle beyond the mechanical stop described above. This feature allows the needle to be advanced to extend beyond the dilator under the control of the physician. In any event, the ultimate distance the needle may be displaced is dependent upon the dimensions of the needle stop mechanism.

Sheath/Dilator Advance Mechanism

Upon completion of the septal puncture, and after the needle is advanced through the tissue, the handheld mechanism preferably includes an additional mechanism to facilitate advancement of the sheath and dilator into the left atrium. One embodiment of this concept utilizes an extension on the distal end of the needle hub which can push the sheath and dilator hub forward. This allows the physician to advance the dilator and sheath over the needle with more stability and control.

In accordance with the present invention, these features and mechanisms are combined to provide an improved cooperative handle assembly for use in transseptal catheterization procedures utilizing a sheath assembly, a dilator assembly and a needle assembly comprising a sheath hub, a dilator hub removably connected to the sheath hub, a needle hub removably connected to the dilator hub, and a needle advancement mechanism adapted to cooperate with the needle assembly, whereby the needle advancement mechanism allows for selective advancement of the needle assembly from a position within a dilator to a position external to the dilator.

Additionally, the present invention provides for a method for manufacturing a handle assembly comprising the following steps: providing a sheath hub, a dilator hub, and a needle hub; removably connecting the dilator hub to the sheath hub; removably connecting the needle hub to the dilator hub; disposing a needle assembly at least partially within the needle hub; and connecting a needle advancement mechanism to the needle assembly, whereby the needle advancement mechanism allows for selective advancement of the needle assembly from a position within a dilator to a position external to the dilator.

Further, the present invention provides for a method for transseptal catheterization utilizing a hand assembly having a removably connected sheath hub, a dilator hub and a needle hub comprising the following steps: locating a needle assembly operably connected to a needle displacement mechanism proximate a targeted area of tissue; advancing the needle assembly by activating the needle displacement mechanism; puncturing a targeted area of tissue with the needle assembly; separating the dilator hub from the needle hub; and advancing the dilator hub and the distal end of the dilator through the punctured tissue area.

The present invention provides a number of advantages, including, for example, provision of an intuitive, inter-locking proximal handle which organizes components and makes them easy to manipulate. The present invention improves current transseptal puncture procedures by: (1) safely and reliably locating the tip of the needle within the dilator; and (2) reducing procedural complexity by simplifying the proximal end of the current tool set, allowing the physician to focus on the other aspects of the procedure. The present invention includes the additional advantage of including a mechanical stop to prevent unintentional advancement of the needle. Further advantageous safety features include a release button for advancement of the needle.

The foregoing and other aspects, features, details, utilities, and advantages of the present invention will be apparent from reading the following description and claims, and from reviewing the accompanying drawings.

BRIEF DESCRIPTION OF THE DRAWINGS

FIGS. 13D and E show cross-sectional views of the needle hub assembly of the tenth embodiment identifying the spring-biased needle advancement mechanism as well as the transverse, spring-biased needle lock button.

DETAILED DESCRIPTION OF THE INVENTION

The instant invention relates to improved hand assemblies and methods combining a number of the separate devices used in transseptal catheterization procedures, including sheaths, dilators, and needle assemblies (including a puncture device and a stylet, for example). The hand assemblies provide cooperating members that reduce the overall complexity and increase safety of transseptal catheterization procedures.

Figure 1:
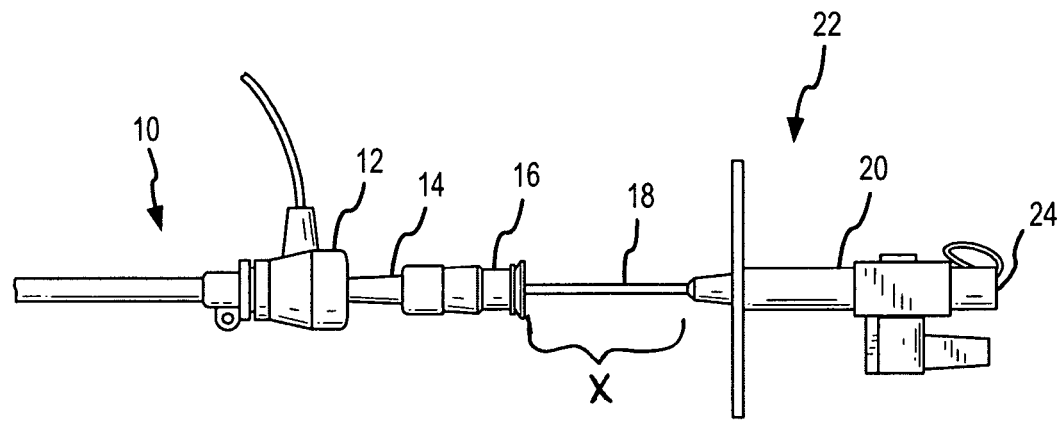
FIG. 1 identifies three common components currently used in transseptal procedures, including a sheath, a dilator, a needle assembly including a stylet. The needle assembly is disposed within an inner lumen of the dilator. Both the dilator and the needle assembly are disposed within the inner lumen of the sheath.

As shown in FIG. 1, typical transseptal procedures utilize at least three separate common components, namely a sheath 10, a dilator 14, and a needle assembly 22 including a stylet 24. The needle assembly 22 is disposed within an inner lumen of the dilator 14. Both the dilator 14 and the needle assembly 22 are disposed within the inner lumen of the sheath 10.

The present invention is directed to embodiments that combine these three separate components into cooperative hand assemblies 100 with a number of structural and operational benefits adding to increased safety and ease of use. The hand assemblies are configured for use with known catheterization assemblies such as those used in transseptal procedures, which typically include a sheath, a dilator, and a puncture assembly, such as a needle assembly. Generally, the present invention comprises cooperatively, a sheath hub 102, a dilator hub 104, and a puncture assembly hub 106 (referred to herein for purposes of example only as a needle hub).

The various hubs, that together form the handle assembly 100, are cooperatively configured and removably connectable through any mechanical device such as a latch, a biased latch, snap assemblies, or any similar removable connection known to those of skill in the art. The hand assembly further comprises a needle advancement mechanism 108 allowing for selective advancement 108 of the needle to various positions, including a retracted position within the distal end of the dilator and an extended position external to the dilator for puncture procedures. The needle advancement mechanism 108 may be a sliding mechanism, a lever mechanism, a roller mechanism, a plunger mechanism, or any other mechanism known to those of skill in the art.

The needle advancement mechanism 108 may further include a locking mechanism to safely maintain the needle in a desired position during use, either in the retracted or extended position. Additionally, the hand assembly 100 may further comprise at least one spacing mechanism for maintaining the various aspects of the assembly, for example the puncture assembly, at predetermined positions during use. Further, the handle assembly may further include additional features such as one-way, two-way, or three-way valves for introduction of fluids, such as, contrast or saline fluids, or for pressure monitoring and safety devices. The handle assembly also may include safety mechanisms, such as a stylet retraction rod, to further prevent against unwanted damage during the procedure.

The materials used to manufacture the handle assemblies are well known to those of skill in the art, and include, for example, injection moldable biocompatible plastics and the like. Particular materials deemed suitable include polyether block amides (sold commercially under the tradename Pebax™), polyurethane, polycarbonate, ABS and polymers with similar properties.

The various aspects of the present invention are described in more detail below in connection with the accompanying Figures for purposes of example. It is contemplated that virtually any of the individual features discussed below could be incorporated in any combination, in accordance with the present invention.

Figure 2:
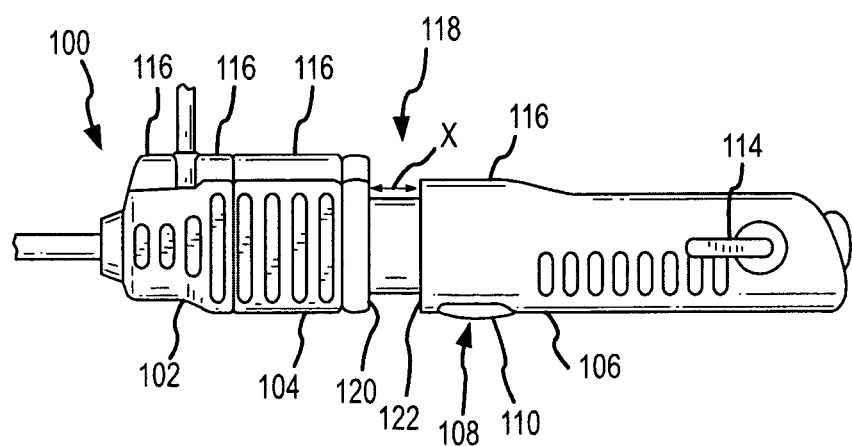
FIG. 2 is a side view of an improved handle assembly in accordance with a first embodiment of the present invention having cooperating hub members for the sheath, dilator and needle assemblies used in transseptal procedures and a needle/stylet stop mechanism between the dilator hub and the needle hub.
Figure 3:
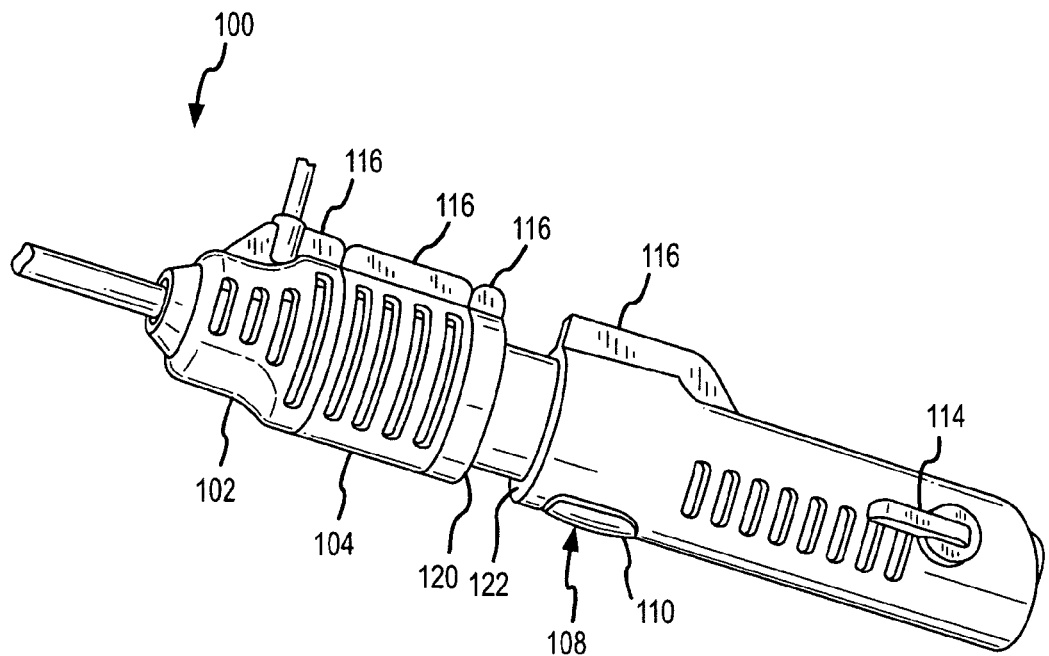
FIG. 3. is a perspective view of the handle assembly shown in FIG. 2 showing the elliptical cross-sectional shape of the various hub assemblies.
Figure 4:
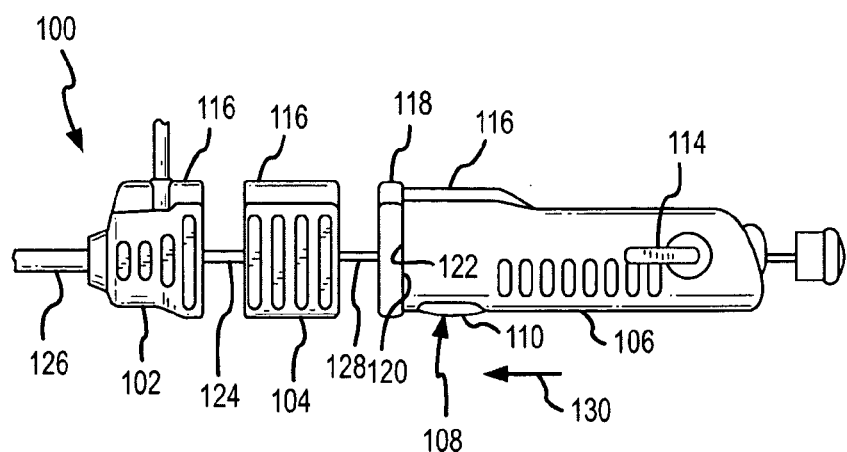
FIG. 4 is a side view of the embodiment in FIGS. 2 and 3 in which the cooperating hubs have been separated and the needle hub has been advanced forward to reach the needle stop assembly.

For example, FIGS. 2, 3 and 4 identify an improved handle assembly in accordance with a first embodiment of the present invention. The handle assembly has cooperating hub assemblies for the sheath 102, dilator 104 and needle assemblies 106 used in transseptal procedures. The hub assemblies of each of these components are preferably preformed having corresponding removably attachable locking mechanisms (not shown). The locking mechanisms include for example, spring or lever biased latches for removable coupling. The assembly further has a two-way adjustable valve 114 disposed within needle hub assembly 106. At least one of the hub assemblies further includes an orientation member 116, e.g., a fin, that serves to visually identify the orientation of the particular assembly inside the body and to help maintain the proper orientation of the members during a transseptal procedure. The configuration of the hub assemblies themselves may also be configured to allow for visual identification of the orientation of the assemblies within the body, e.g., in an elliptical cross-sectioned shape (as shown in FIG. 3).

Additionally, the first embodiment of FIGS. 2, 3 and 4 includes a needle stop mechanism 118 provided between the dilator hub 104 and the needle hub 106. The needle stop mechanism 118 is designed such that in the position shown in FIG. 2, the needle is contained at a predetermined position within the distal end of the dilator. In the default position, the needle stop mechanism 118 removably engages the dilator hub 104 and the needle hub 106 and maintains a predetermined distance between these hubs, corresponding to a desired distance between the distal end of the dilator and the distal end of the needle assembly. The needle stop mechanism 118 is removably coupled to needle hub 106 via a latch assembly 110 having a needle advance mechanism 108, e.g., button disposed on the outer surface of the needle hub 106. As shown in FIGS. 2 and 3, in order to advance the needle towards the distal end of the dilator, a physician (or any user) simply activates the needle advance mechanism 108, e.g., presses the button. Upon activation of the button, the needle hub is released from the needle stop mechanism 118 and the dilator hub 104, thereby allowing for advancement of the needle assembly within the dilator a maximum distance corresponding to the distance between a needle stop interface 120 on the needle stop mechanism 118 and the distal end of the needle hub (represented as the distance "X" in FIG. 2). This mechanism 118 provides for safe operation of the needle assembly by preventing movement of the needle assembly until desired activation by a user and further provides for accurate movement to a desired piercing position when the needle hub 106 is advanced to a point where the distal end 122 abuts the needle stop interface 120.

The sheath hub 102 and the dilator hub 104 also have a corresponding snap lock feature that allows for temporary coupling of the two hub assemblies. FIGS. 2 and 3 show the dilator and sheath hubs in a locked position. After the puncture step is effected by the needle 128, as shown in FIG. 4 (or at any other desirable phase of the procedure), these assemblies may be separated from the needle stop assembly, and each other, to allow for insertion of either, or both, the dilator and the sheath across the punctured interatrial septum (see FIG. 4).

Figure 5A:
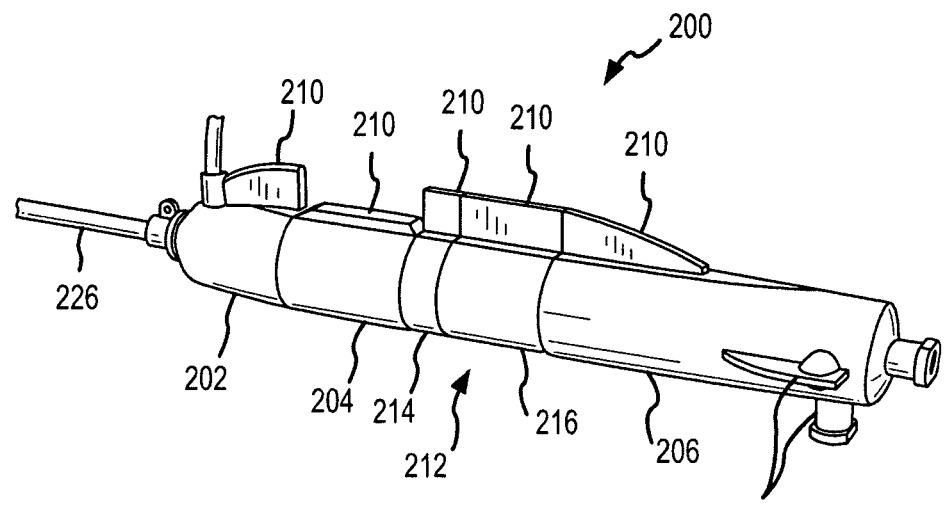
FIG. 5A shows a perspective view of an improved handle assembly in accordance with a second embodiment of the present invention.

FIGS. 5A and B identify an improved handle assembly in accordance with a second embodiment of the present invention. The handle assembly 200 has cooperating hub assemblies for the sheath 202, dilator and needle assemblies 206 used in transseptal procedures. The hub assemblies of each of these components are preferably preformed having corresponding removably attachable locking mechanisms (not shown). The locking mechanisms include for example, snap-fit assembly, or spring or lever biased latches for removable coupling. The assembly further has a two-way or three-way adjustable valve 208 disposed within needle hub assembly 206. At least one of the hub assemblies further includes an orientation member 210, e.g., a fin, that serves to visually identify the orientation of the particular assembly inside the body and to help maintain the proper orientation the members during a transseptal procedure.

Additionally, the dilator hub 204 and the needle hub 206 are separated by at least one removable spacer 212. In this particular embodiment there are two spacers 212 present, a first spacer 214 located proximate the dilator hub 204, and a second spacer 216 located near the needle hub 206 at its distal end. The first spacer 214 is configured to allow for insertion of the stylet 218 (See FIG. 5B) a predetermined distance towards the distal end of the dilator 220. It is also contemplated that the stylet 218 could be removed, and therefore, removal 228 of the first spacer 214 would allow for advancement 222 of the needle to the first predetermined position. In the instance where the stylet 218 is not removed, removal 220 of the first spacer 214 and subsequent advancement 222 of the needle hub 206 would result in the stylet 218 extending out the distal end of the dilator (a generally undesirable action). Additionally, the second spacer 216 may be removed, in which case, the needle hub 206 can be advanced forward a predetermined distance toward the distal end of the dilator. When the second spacer is removed, the needle assembly may be advanced forward into a puncture position outside the distal end of the dilator for puncture of the interatrial septum.

Figure 5B:
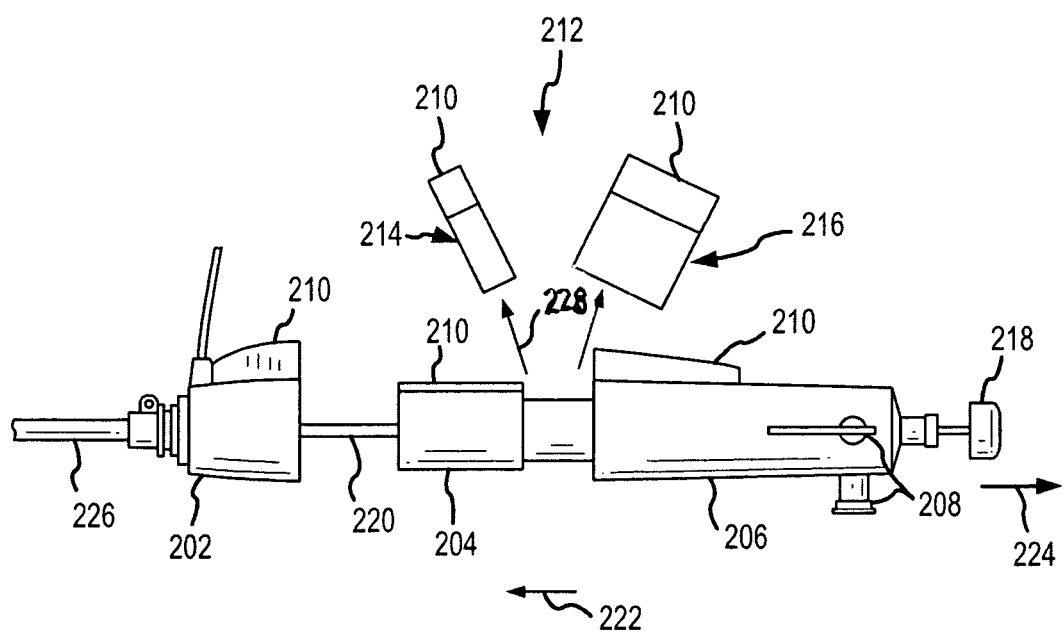
FIG. 5B shows a side view of a second embodiment of the present invention in which the cooperating hubs have been separated and the needle hub has been advanced forward a predetermined distance thereby moving the stylet a corresponding distance in the opposite direction.

The sheath hub and the dilator hub shown in FIGS. 5A and B also have corresponding snap lock features (not shown) that allows for temporary coupling of the two hub assemblies. As shown in FIG. 5B, after the puncture step is effected (or at any other desirable phase of the procedure), these assemblies 202, 204 may be separated from the needle hub assembly 206, and each other, to allow for insertion of either, or both, the dilator 220 and the sheath 226 across the punctured interatrial septum.

Figure 6A:
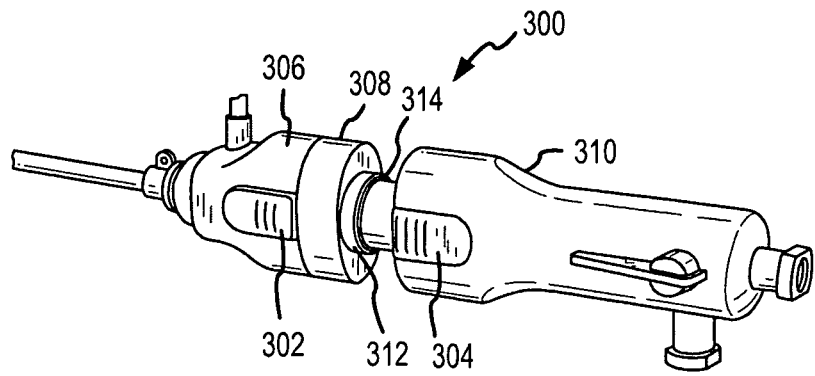
FIG. 6A shows a perspective view of an improved handle assembly in accordance with a third embodiment of the present invention.
Figure 6B:
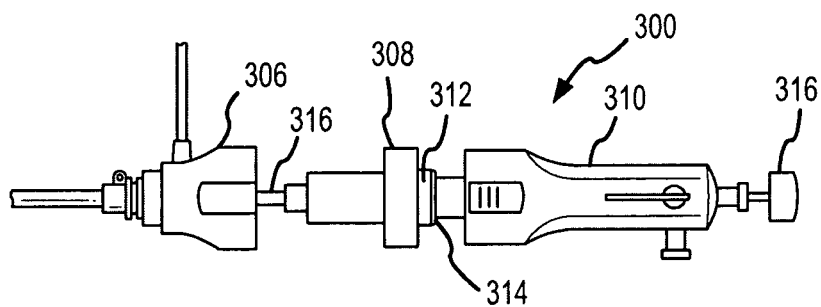
FIG. 6B is a side view of a third embodiment of the present invention in which the cooperating hubs have been separated.
Figure 6C:
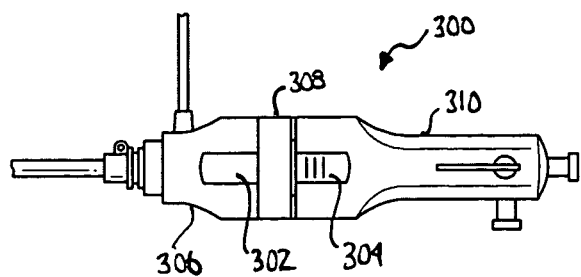
FIG. 6C is a side view of a third embodiment of the present invention in which the needle hub has been advanced forward to abut the needle stop mechanism, thereby extending the distal tip of the needle beyond the distal tip of the sheath and/or dilator.

FIG. 6A-6C identify an improved handle assembly in accordance with a third embodiment of the present invention. The handle assembly 300 has many similar features to those described in FIGS. 2-4. In addition, the handle assembly in 300 further includes two button-release assemblies 302, 304, one for removably coupling the sheath hub and the dilator hub and the other for coupling the needle hub to the needle stop mechanism 312. Alternatively, the needle hub 310 may comprise a ridge 314 (in this case an annular ridge) surrounding the distal portion of the needle hub, or any other structure that applies tactile resistance. This ridge 314 interfaces with the proximal portion of the needle stop mechanism 312 and serves to provide a temporary stop for the needle assembly 310. Thus, the assembly FIG. 6A is shown in the needle stop position. In use, the user inserts the needle assembly 310 to a desired predetermined position within the dilator 316 by pressing the assembly 310 forward until the ridge 314 meets the proximal end of the stop mechanism 312. At this point, the user receives tactile feedback that the needle is in the proper position. At a point where the user desires to advance the needle into a puncture position extending beyond the dilator 316, he may do so by pressing forward with a greater force such that the ridge 314 passes through the proximal end 312. In the embodiment of FIG. 6A-6C, the shape of the hub assemblies themselves and the corresponding placement of the button-release mechanisms serve the dual purpose of being orientation members for visual confirmation of the orientation of the particular assembly inside the body and to help maintain the proper orientation the members during a transseptal procedure. Again, these orientation members are very valuable to physicians during procedures, such as transseptal puncture procedures, where curved needles are routinely utilized.

FIG. 6B shows a side view of the various hub assemblies, separated from each other, as similarly shown in and discussed with respect to FIG. 4 above. Further, shown is a stylet 316 after use in connection with the assembly. FIG. 6B also shows the ridge 314 that provides the additional benefit of tactile feedback during use by a physician. FIG. 6C further identifies the hand assembly being in its fully advanced, or puncture, position.

Figure 7A:
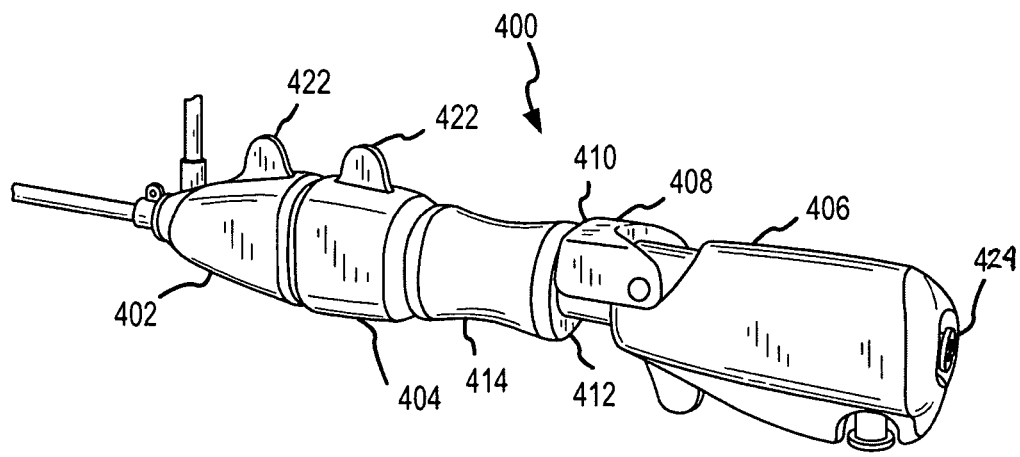
FIG. 7A shows a perspective view of an improved handle assembly in accordance with a fourth embodiment of the present invention having a safety latch assembly to prevent unintended advancement of the needle hub.
Figure 7B:
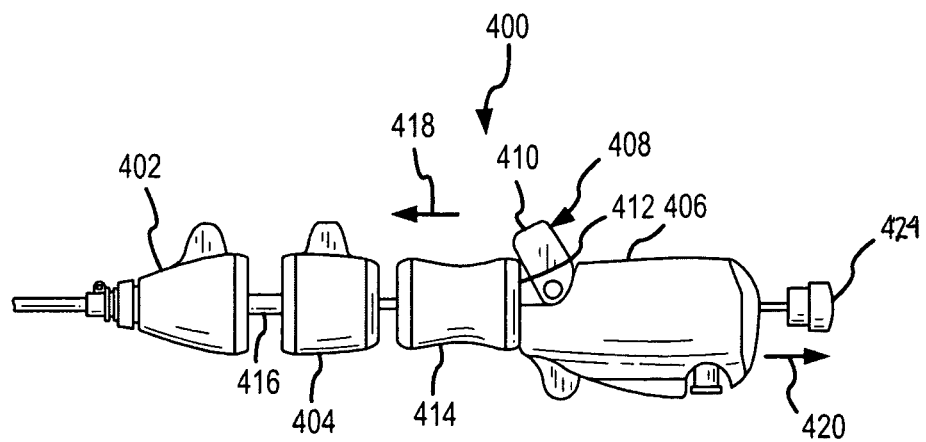
FIG. 7B shows a side view of a fourth embodiment of the present invention in which the cooperating hubs have been separated and the needle hub has been advanced forward a predetermined distance thereby extending the distal tip of the needle beyond the distal tip of the sheath and/or dilator.

FIG. 7A-7B identifies an improved handle assembly in accordance with a fourth embodiment of the present invention. The handle assembly 400 according to this embodiment has a sheath hub 402 located at the distal end of the assembly 400, a dilator hub 404 proximate the sheath hub, and a needle hub 406 located at the proximal end of the assembly. The hub assemblies of each of these components are preferably preformed and may have corresponding removably attachable locking/mating mechanisms. The assembly further comprises a safety latch 408 as a needle lock mechanism of a predetermined length that is pivotally connected to the needle hub 406, such that when it is in a locked position (see FIG. 7A), the distal end 410 of the safety latch 408 abuts the proximal end 412 of the front portion 414 of the needle hub 406. In this position, the needle assembly 406 is prevented from being advanced forward, thereby preventing the distal end of the needle from being extended beyond the distal end of the dilator 416. This mechanism thereby provides another structural safety feature preventing unnecessary punctures and the like when the assembly is used in the human body.

This fourth embodiment further includes a stylet displacement rod (not shown) disposed within the needle hub extending through the entire needle hub and terminating at a distal portion. The length of the stylet displacement rod is preset to abut with a corresponding portion of the dilator hub 404 when the needle hub 406 is advanced toward the distal end of the assembly. The stylet displacement rod is slidably fixed within the assembly such that when the needle hub 406 is advanced forward 418 and the displacement rod abuts the dilator hub 404, the stylet 424 is displaced a preset position in a direction away 420 from the proximal end of the assembly 400. This mechanism serves to withdraw the distal end of the stylet 424 a preset distance from the end of the dilator, further providing safety benefits during operation of the assembly.

In addition, at least one of the hub assemblies further includes an orientation member 422, e.g., a fin, that serves to visually identify the orientation of the particular assembly inside the body and to help maintain the proper orientation the members during a transseptal procedure. The orientation member could also be a visible mark, an indentation, a raised projection or the like. Alternatively, the shape of the various hubs may provide the orientation information necessary.

Figure 8A:
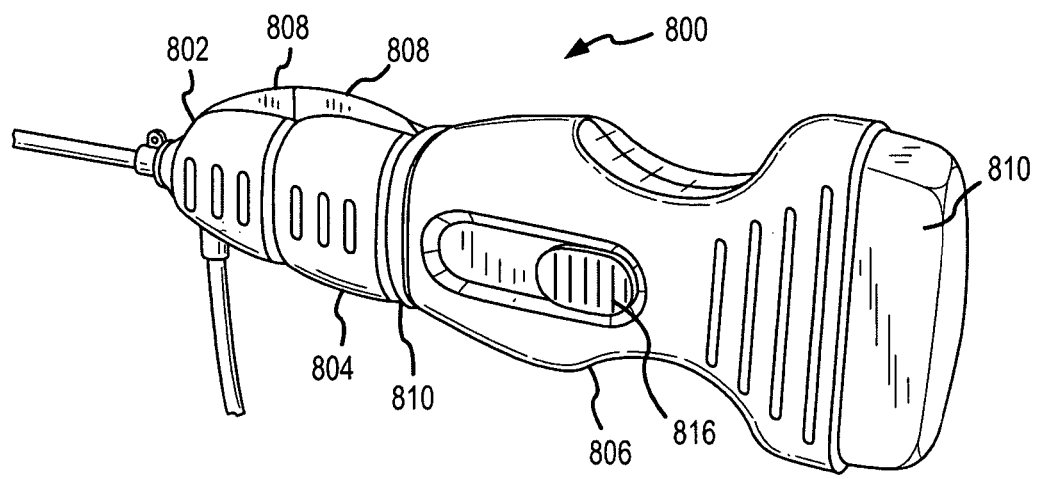
FIG. 8A shows a perspective view of an improved handle assembly in accordance with a fifth embodiment of the present invention.
Figure 8B:
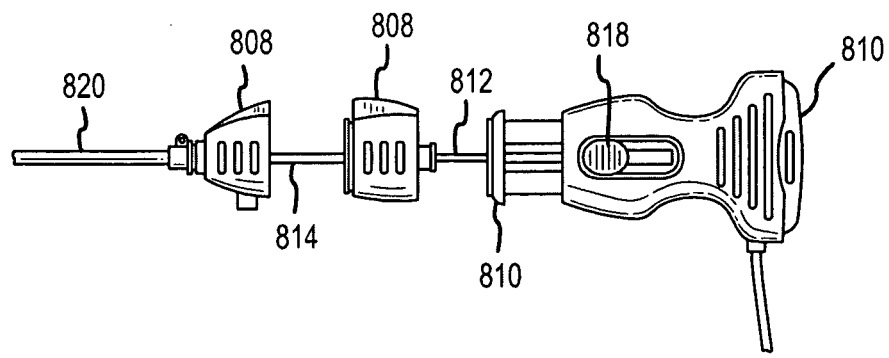
FIG. 8B shows a side view of an improved handle assembly in accordance with a fifth embodiment of the present invention in which the cooperating hubs have been separated and both the dilator/sheath advancement mechanism and the needle advance mechanism are shown in their fully advanced position.

FIGS. 8A-8B identify an improved handle assembly 800 in accordance with a fifth embodiment of the present invention. In this embodiment, the handle assembly 800 has cooperating hub assemblies for the sheath 802, dilator 804 and needle assemblies 806 used in transseptal procedures. The hub assemblies of each of these components are preferably preformed having corresponding removably attachable locking mechanisms, such as a snap-fit assembly. The assembly may also include a two-way adjustable valve (not shown) disposed within the needle hub assembly 806. At least one of the hub assemblies further includes an orientation member 808, e.g., a fin, that serves to visually identify the orientation of the particular assembly inside the body and to help maintain the proper orientation of the needle and other pieces during a transseptal procedure.

A needle advancement device 810 is located at the proximal end of the needle hub 806 and is operably connected to the needle assembly 812 for advancement of the needle through the dilator 814. The needle advance assembly 810 may be a plunger-type advance and may further be biased such that release of the mechanism results in an automatic retraction of the needle assembly 812. This biased mechanism may include a spring assembly (not shown). A dilator/sheath advancement mechanism 816, e.g., a button is provided on the side of the needle hub 806 for advancement of the sheath/dilator assemblies 802/804 by the user in operation. In the advanced position 818, the sheath 806 and dilator hubs 804 are separated form the needle assembly 806, thereby allowing for the sheath 820 and/or dilator 814 to be extended over the needle assembly 812 and through the punctured tissue. This mechanism allows for added safety during use.

Figure 9A:
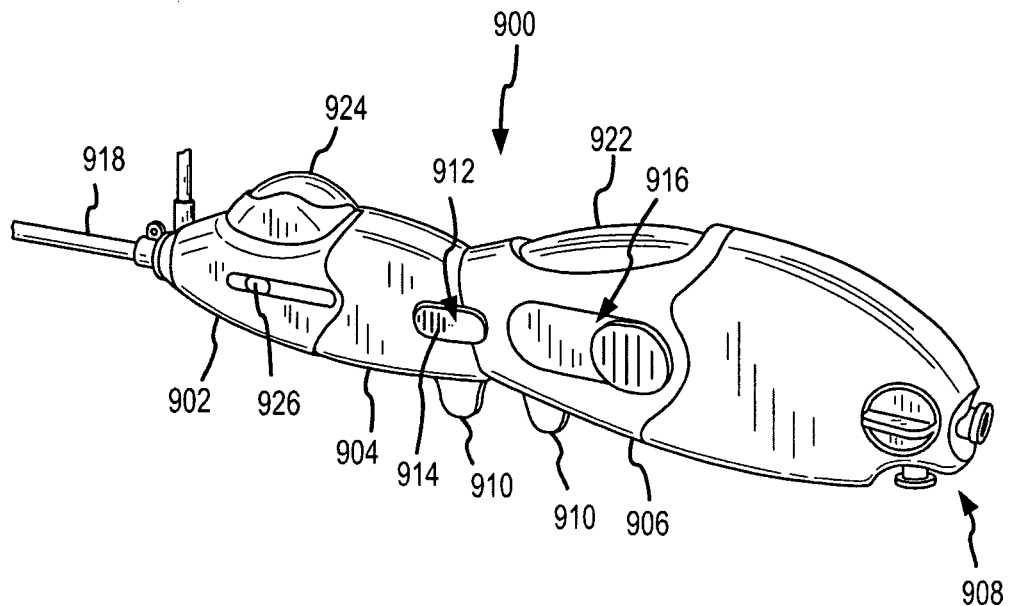
FIG. 9A shows a perspective view of an improved handle assembly in accordance with a sixth embodiment of the present invention having the additional features of a shaft or dilator deflection mechanism and a needle position indicator.
Figure 9B:
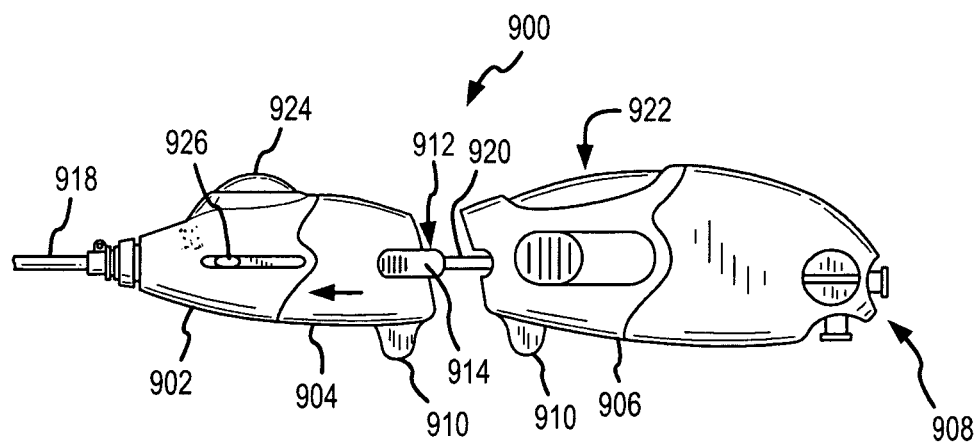
FIG. 9B shows a side view of an improved handle assembly in accordance with a sixth embodiment of the present invention in which the cooperating dilator and needle hubs have been separated.

FIG. 9A-9B identify a sixth embodiment of the handle assembly according to the present invention. The handle assembly according to this embodiment has a sheath hub 902 located at the distal end of the assembly, a dilator hub 904 proximate the sheath hub 902, and a needle hub 906 located at the proximal end of the assembly 900. The assembly 900 further has a three-way adjustable valve 908 disposed within needle hub 906 assembly. At least one of the hub assemblies further includes an orientation member 910, e.g., a fin, that serves to visually identify the orientation of the particular assembly inside the body and to help maintain the proper orientation of the various pieces during a transseptal procedure.

The hub assemblies of each of these components are preferably preformed in corresponding shapes and may have corresponding removably attachable locking mechanisms 912. For example, the assembly comprises a connection mechanism 912 that removably couples the dilator hub 904 to the needle hub 906. The connection mechanism may be a latch mechanism with a corresponding push button 914 for manual release of the hub connection.

The needle hub 906 further comprises a sheath/dilator advancement mechanism located on the side of the hub for manual separation of the sheath/dilator to facilitate advancement of the sheath 918 and/or dilator over the needle assembly 920. When activated, the sheath 902 and dilator hubs 904 may be moved distally, thereby advancing the sheath 908 and dilator (not shown) over the needle 920 inside the body. Additionally, the needle hub 906 also includes a needle advancement mechanism 922 shown in FIG. 9 as a button on the upper portion of the needle hub 906. In the unbiased position, the needle assembly 920 remains at a predetermined position within the dilator. Upon activation of the needle advancement mechanism, the distal portion of the needle assembly advances a predetermined portion beyond the distal end of the dilator for use in puncturing the interatrial septum. While the embodiment shows a push-button mechanism for advancing the needle 920 and separating the hub assemblies, it is contemplated that any similar mechanism may be used, including, for example, a biased roller mechanism or a sliding mechanism. Moreover, it is contemplated that these mechanical safety features can be similarly implemented by placing them, in whole or part, within the other hub assemblies.

The embodiment shown in FIG. 9 preferably further includes a deflection mechanism configured to manipulate a steerable sheath assembly. In this embodiment, the deflection mechanism 924 is shown as a rolling mechanism located on the sheath hub 902. It is however contemplated that any similar steering mechanism known to those of skill in the art could be used, and could be placed at any appropriate position on the device 900. It is further contemplated that a similar device could be utilized in connection with a steerable dilator or a steerable needle.

Additionally, the sixth embodiment may include a position indicator 926 (shown on the side of the sheath assembly in FIG. 9). This position indicator is operably connected to the needle assembly 920 to provide visual confirmation of the position of the needle assembly 920 within the device, dilator, and/or the sheath within the body. This indicator provides an additional safety measure by allowing for quick confirmation by the user that the needle assembly 920, dilator and/or sheath is in the desired position. While this position indicator 926 is shown on the sheath hub 902 in FIG. 9, it is contemplated that it could be placed at any appropriate position on the handle assembly 900. It is further contemplated that the position indicator 926 could be an electronic position indicator, such as an LED display operably connected to the needle assembly 920 to provide various visual signals depending on the position of the needle assembly 920. Alternatively, the indicator 926 could be an audible indicator operably connected to provide various signals depending upon the position of the needle assembly.

Figure 10A:
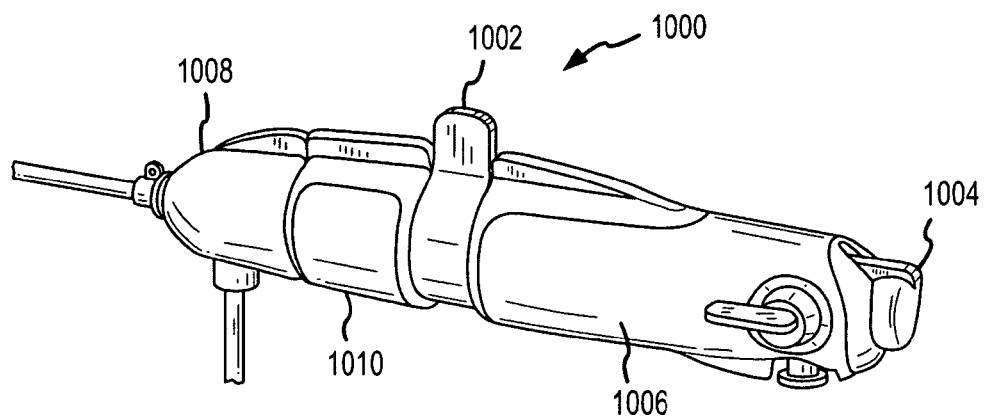
FIG. 10A shows a perspective view of an improved handle assembly in accordance with a seventh embodiment of the present invention having three hub assemblies and a single spacer between the dilator hub and the needle hub.
Figure 10B:
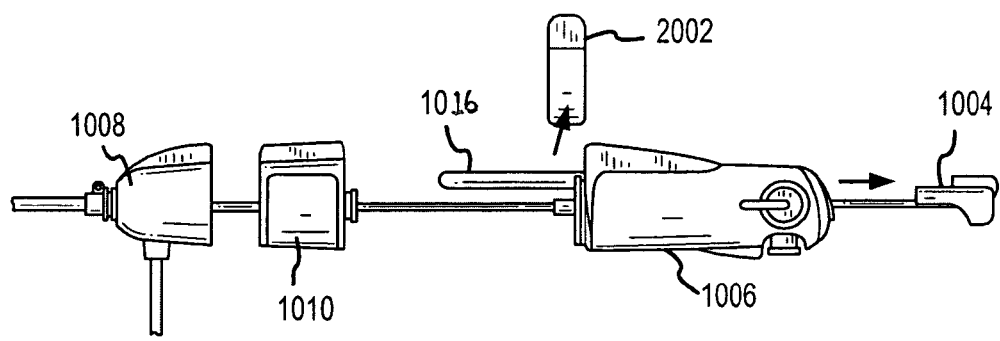
FIG. 10B shows a side view of an improved handle assembly in accordance with a seventh embodiment of the present invention in which the cooperating hubs have been separated further disclosing the presence of a stylet stop/displacement mechanism.

FIGS. 10A-10B identify a seventh embodiment of the handle assembly 1000 according to the present invention incorporating the common elements of a sheath hub 1008, dilator hub 1010, and needle hub 1006. This embodiment combines the removable spacer 1002 feature described above with respect to FIGS. 5A-5B and further includes the stylet stop/displacement mechanism 1016 described above with respect to FIGS. 7A-7B. This embodiment thus provides the joint benefits of preventing unnecessary advancement of the needle assembly 1006 until the spacer 1002 is removed, while also providing for withdrawal of the stylet 1004 a predetermined portion toward the proximal end of the assembly when the needle hub is advanced forward. As shown in FIG. 10B, the stylet 1004 is removable from the assembly 1000.

Figure 11A:
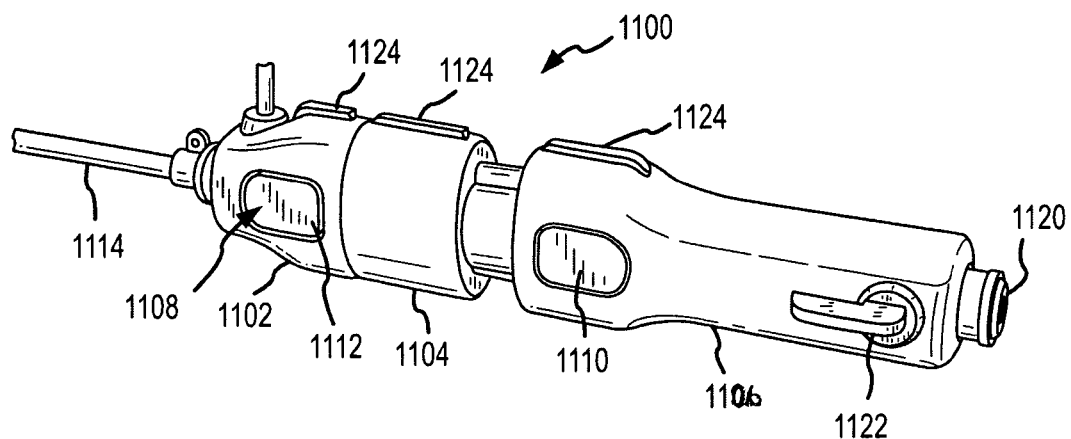
FIG. 11A shows a perspective view of an improved handle assembly in accordance with an eighth embodiment of the present invention having three hub assemblies that are removably attached to one another through two button/latch assemblies.
Figure 11B:
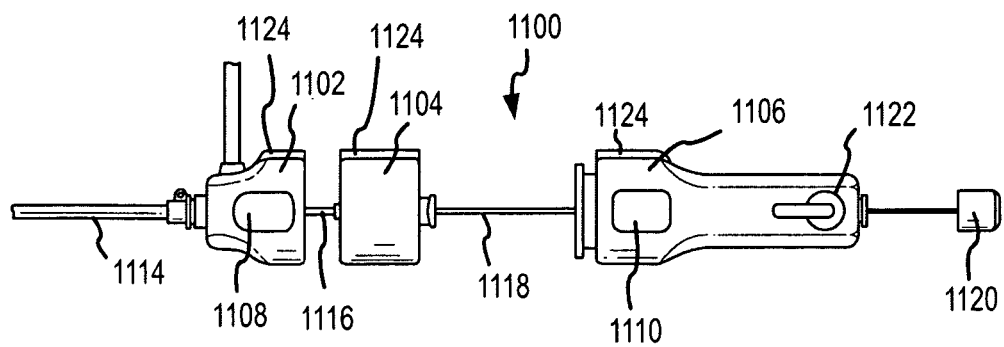
FIG. 11B shows a side view of an improved handle assembly in accordance with an eighth embodiment of the present invention in which the cooperating hubs have been separated.

FIGS. 11A-11B identify an eighth embodiment of the handle assembly 1100 according to the present invention. The embodiment of FIG. 11 provides similar structural components as that described with respect to FIG. 6 above incorporating the common element of a sheath hub 1102, dilator hub 1104 and needle hub 1106. In this embodiment, the sheath hub 1102 and the needle hub 1106 assemblies are removably attached to the dilator hub 1104 through biased latch 1108. Further provided, is a needle stop mechanism 1110. When the button shown on the side of the sheath hub 1102 is pressed, the sheath 1114 is uncoupled from the dilator 1116, allowing for independent adjustment of the sheath 1114 from the dilator 1116. Again, the embodiment shown in FIG. 11 provides for a removable stylet 1120 and an adjustable valve 1122, disposed in the needle hub 1106. Additionally, as shown in FIG. 11A, orientation indicators 1124 are included for identification of the position of the sheath 1114, dilator 1116, and needle 1118 assemblies during use.

Figure 12A:
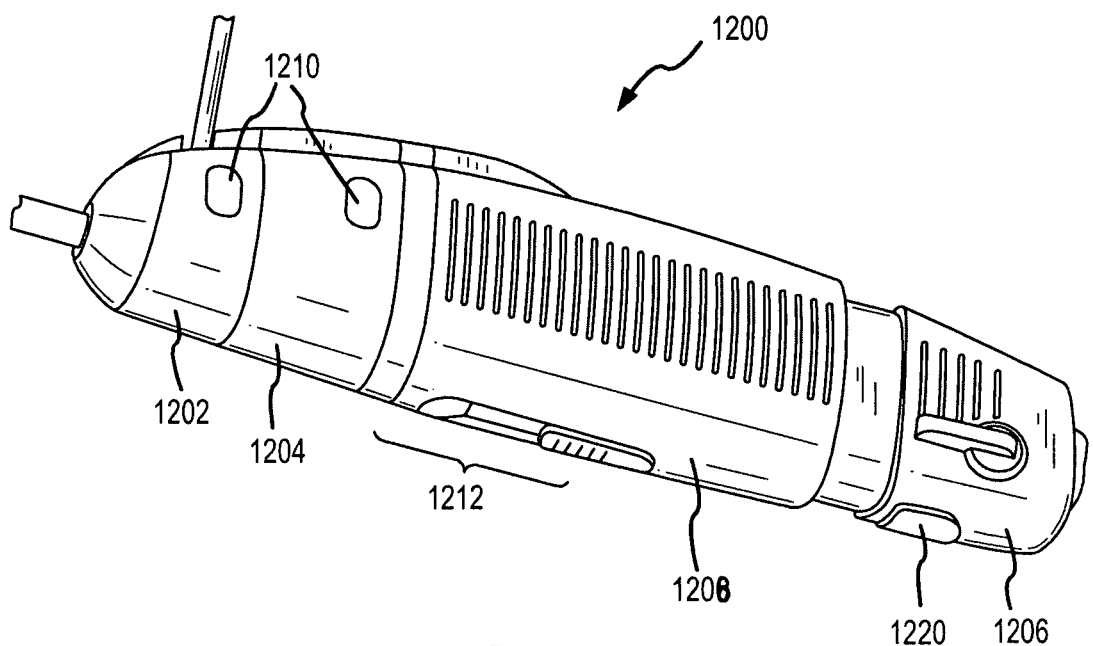
FIG. 12A shows a perspective view of an improved handle assembly in accordance with a ninth embodiment of the present invention having three cooperative hub assemblies and an elongated handle portion disposed between the needle hub and the dilator hub.
Figure 12B:
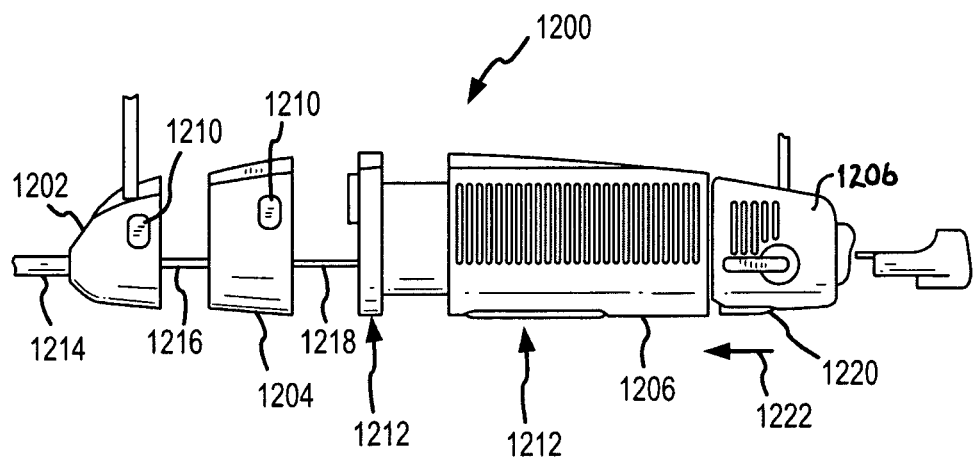
FIG. 12B shows a side view of an improved handle assembly in accordance with a ninth embodiment of the present invention in which the cooperating dilator and sheath hubs have been separated and the needle advancement mechanism is in its advanced position.

FIGS. 12A-12B identify a ninth embodiment of the handle assembly 1200 according to the present invention. This embodiment includes a sheath hub 1202, a dilator hub 1204, a needle hub 1206, and an elongated handle body 1208 disposed between the dilator hub 1204 and the needle hub 1206. This embodiment includes the biased latch assemblies 1210 described above for removably connecting the various hub assemblies 1202, 1204 together until separation is desirable. This embodiment includes a slidable sheath/dilator advance mechanism 1212 for separating the dilator 1204 and sheath hubs 1202 from the handle body 1208. When advanced forward, the sheath 1214 and dilator 1216 are advanced over the needle 1218 into the left atrium. Additionally, a needle advancement 1220 assembly is included within the needle hub assembly 1206 for pressing the needle assembly forward into a puncture position when desired by the user. When activated by the user, the needle hub 1206 can be advanced 1222 as a whole a predetermined distance until the distal end of the needle assembly abuts with the proximal end of the elongated handle body 1208 (as shown in FIG. 12B). This configuration further prevents from extending the needle assembly a distance too far outside the distal portion of the dilator.

Figure 13A:
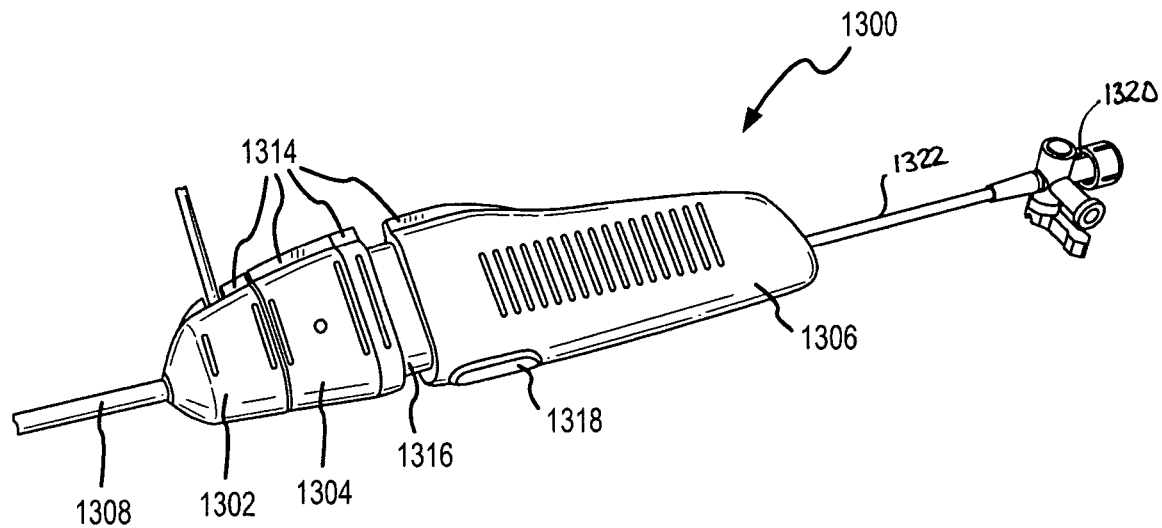
FIG. 13A shows a perspective view of an improved handle assembly in accordance with a tenth embodiment of the present invention having three hub assemblies cooperatively attached via snap-fit engagements and having an external three way valve assembly attached to the needle assembly via a flexible tube.
Figure 13B:
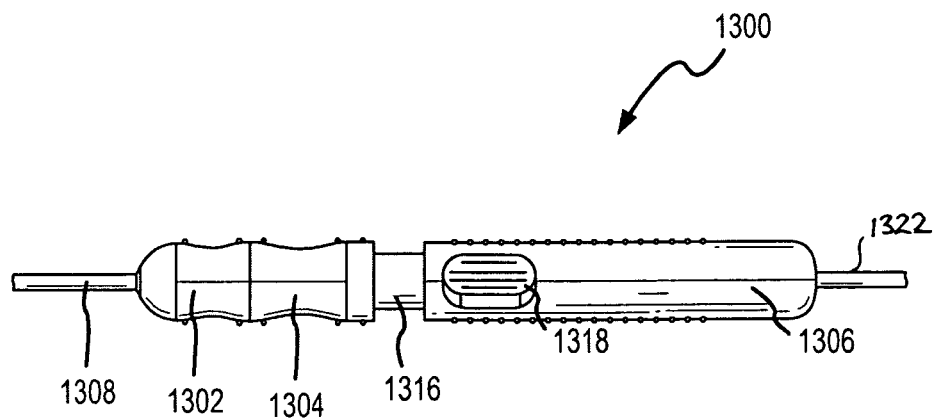
FIG. 13B is a bottom view of an improved handle assembly in accordance with a tenth embodiment of the present invention identifying indented areas, or detent areas, on the sheath and dilator hubs for increased usability and a transverse needle lock mechanism for activating the needle assembly.
Figure 13C:
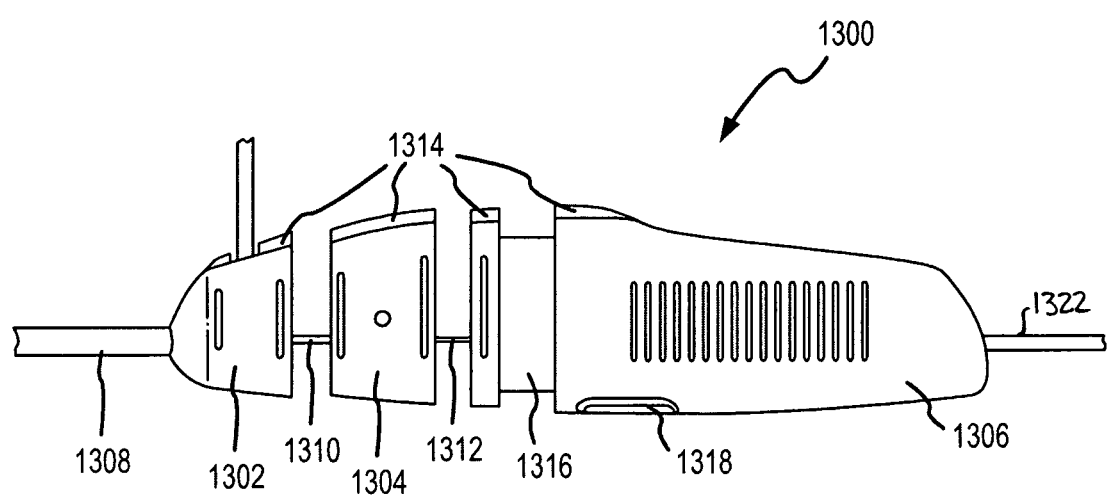
FIG. 13C shows a side view of an improved handle assembly in accordance with a tenth embodiment of the present invention in which the cooperating hubs have all been separated and the needle advancement mechanism is in its retracted position.

FIGS. 13A-13C identify a further preferred embodiment according to the present invention. In this embodiment, the handle assembly 1300 includes a sheath hub 1302, a dilator hub 1304, and a needle hub 1306. All three hubs are removably connected to each other through cooperating snap-fit mechanisms (e.g., 1328) which serve to hold the hubs together and further to accurately position the hubs and accordingly the sheath 1308, dilator 1310 and needle assemblies 1312 for use. To further facilitate orientation, the handle assembly 1300 is shaped in a generally elliptical cross-section and further includes orientation members 1314, e.g., fins or other visible markings.

As shown in FIGS. 13A-13E, the assembly 1300 further comprises a needle stop mechanism 1316 that is configured to allow for the needle assembly to be advanced a predetermined distance upon activation of a needle unlock mechanism 1318. The needle stop mechanism 1316 is biased, in this case via a spring 1324 in a first, retracted, position (shown in FIG. 13A). The needle unlock mechanism 1318 is operably connected to the needle stop mechanism 1316 such that upon activation of the needle unlock mechanism 1318 (preferably in a direction perpendicular to the direction of advancement of the needle as shown in FIG. 13B) the needle hub and needle assembly can be advanced forward the preset distance established by the needle stop mechanism, thereby advancing the needle the appropriate preset distance for the particular procedure. After the needle has been removed from the dilator (or at least retracted a sufficient distance), the needle unlock assembly, upon a second activation, or simple release of, the needle lock button, would reset the needle stop mechanism 1316 to the pre-procedure state. This is accomplished via a second biasing mechanism, shown as a spring 1326 operatively connected to the needle unlock assembly 1318.

FIG. 13A further identifies an external three-way valve 1320 operatively attached to the needle hub 1306 via a flexible tube 1322. The structure of the valve and flexible tube provide further benefits to the present invention, such as allowing for individuals other than the individual operating the handle assembly during a procedure to assist in delivering fluids or other devices.

Although numerous embodiments of this invention have been described above with a certain degree of particularity, those skilled in the art could make numerous alterations to the disclosed embodiments without departing from the spirit or scope of this invention.

All directional references (e.g., upper, lower, upward, downward, forward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An inter-locking handle assembly for use in transseptal catheterization procedures utilizing a sheath assembly, a dilator assembly and a needle assembly, the handle assembly comprising:
   a sheath hub;
   a dilator hub slidably and latchably connected to the sheath hub;
   a needle hub slidably and latchably connected to the dilator hub;
   a needle stop mechanism movable relative to at least one of the needle hub or the dilator hub without disconnecting the dilator hub from the needle hub; and
   a needle advancement mechanism adapted to cooperate with the needle stop mechanism, wherein a first actuation of the needle advancement mechanism causes the needle stop mechanism to move in a manner such that the needle assembly advances from a position within a sheath or a dilator to a predetermined position external to the sheath or the dilator and a second actuation of the needle advancement mechanism causes the needle stop mechanism to move in a manner such that the needle assembly advances from a position external to at least one of the sheath or the dilator to a predetermined position within the sheath or the dilator.

2. The inter-locking handle assembly of claim 1 further comprising a spacing mechanism adapted to maintain the needle assembly in a predetermined position within the dilator.

3. The inter-locking handle assembly of claim 2 wherein the spacing mechanism comprises at least one removable spacer.

4. The inter-locking handle assembly of claim 1 further comprising at least one orientation member located on at least one of the sheath hub, dilator hub, or needle hub.

5. The inter-locking handle assembly of claim 1 wherein the dilator hub is removably connected to the sheath hub by a latch, a biased latch, or a push button assembly.

6. The inter-locking handle assembly of claim 1 wherein the needle hub is removably connected to the dilator hub by a latch, a biased latch, or a push button assembly.

7. The inter-locking handle assembly of claim 1 wherein the needle advancement mechanism is a slide mechanism.

8. The inter-locking handle assembly of claim 1 wherein the needle advancement mechanism is a roller mechanism.

9. The inter-locking handle assembly of claim 1 wherein the needle advancement mechanism is a lever mechanism.

10. The inter-locking handle assembly of claim 1 wherein the needle advancement mechanism is a plunger mechanism.

11. The inter-locking handle assembly of claim 1 wherein the needle advancement mechanism is disposed within the needle hub.

12. The inter-locking handle assembly of claim 1 wherein the needle advancement mechanism comprises a bias device holding a distal end of the needle assembly within the dilator.

13. The inter-locking handle assembly of claim 1 further comprising a locking mechanism preventing movement of the needle assembly.

14. The inter-locking handle assembly of claim 1 further comprising a valve.

15. The inter-locking handle assembly of claim 1 further comprising a stylet displacement mechanism configured to move a stylet in a direction opposite of the needle assembly upon advancement of the needle advancement mechanism.

16. The inter-locking handle assembly of claim 1 further comprising a needle indicator.

17. The inter-locking handle assembly of claim 1 further comprising a steering mechanism operably connected to at least one of the sheath assembly, dilator assembly, and needle assembly and operable to deflect at least one of the sheath assembly, dilator assembly, and needle assembly.

18. An inter-locking handle assembly for use in transseptal catheterization procedures utilizing a sheath assembly, a dilator assembly and a needle assembly, the handle assembly comprising:

a sheath hub;

a dilator hub slidably and latchably connected to the sheath hub;

a needle hub slidably and latchably connected to the dilator hub;

a needle stop mechanism movable relative to at least one of the needle hub or the dilator hub; and a needle advancement mechanism operable to perform two actuations and adapted to cooperate with the needle stop mechanism, wherein the first actuation of the needle advancement mechanism causes the needle stop mechanism to move in a manner such that the needle assembly advances from a position within a sheath or a dilator to a predetermined position external to the sheath or the dilator and the second actuation of the needle advancement mechanism causes the needle stop mechanism to move in a manner such that the needle assembly advances from a position external to at least one of the sheath or the dilator to a predetermined position within the sheath or the dilator.

19. An inter-locking handle assembly for use in transseptal catheterization procedures utilizing a sheath assembly, a dilator assembly and a needle assembly, the handle assembly comprising:

a sheath hub;

a dilator hub slidably and latchably connected to the sheath hub;

a needle hub slidably and latchably connected to the dilator hub;

a needle stop mechanism movable relative to at least one of the needle hub or the dilator hub when the dilator hub and needle hub are latchably connected to each other; and a needle advancement mechanism adapted to cooperate with the needle stop mechanism, wherein a first actuation of the needle advancement mechanism causes the needle stop mechanism to move in a manner such that the needle assembly advances from a position within a sheath or a dilator to a predetermined position external to the sheath or the dilator and a second actuation of the needle advancement mechanism causes the needle stop mechanism to move in a manner such that the needle assembly advances from a position external to at least one of the sheath or the dilator to a predetermined position within the sheath or the dilator.

\* \* \* \* \*